US010342986B2

(12) United States Patent
Jin

(10) Patent No.: US 10,342,986 B2
(45) Date of Patent: Jul. 9, 2019

(54) FREQUENCY SPECIFIC SENSORY STIMULATION

(71) Applicant: Newport Brain Research Laboratory Inc., Newport Beach, CA (US)

(72) Inventor: Yi Jin, Irvine, CA (US)

(73) Assignee: Kosivana Holdings Limited, Limassol (CY)

(*) Notice: Subject to any disclaimer, the term of this patent is extended or adjusted under 35 U.S.C. 154(b) by 796 days.

(21) Appl. No.: 13/858,617

(22) Filed: Apr. 8, 2013

(65) Prior Publication Data

US 2013/0267759 A1  Oct. 10, 2013

Related U.S. Application Data

(60) Provisional application No. 61/621,389, filed on Apr. 6, 2012, provisional application No. 61/621,399, filed on Apr. 6, 2012.

(51) Int. Cl.
*A61N 2/00* (2006.01)
*A61M 21/00* (2006.01)
*A61M 21/02* (2006.01)

(52) U.S. Cl.
CPC ............. *A61N 2/002* (2013.01); *A61M 21/02* (2013.01); *A61N 2/004* (2013.01); *A61M 2021/0022* (2013.01); *A61M 2021/0027* (2013.01); *A61M 2021/0044* (2013.01)

(58) Field of Classification Search
CPC ................. A61M 21/00; A61M 21/02; A61M 2021/0005; A61M 2021/0022; A61M 2021/0027; A61M 2021/0044; A61M 2021/005; A61M 2021/0061; A61M 2021/0088
See application file for complete search history.

(56) References Cited

U.S. PATENT DOCUMENTS

| 4,282,864 | A  |   | 8/1981  | Pizer |
|---|---|---|---|---|
| 4,289,121 | A  | * | 9/1981  | Kupriyanovich ..... A61M 21/00 600/27 |
| 5,242,376 | A  | * | 9/1993  | Shealy .................. A61M 21/00 600/27 |
| 5,495,853 | A  | * | 3/1996  | Yasushi ................ A61B 5/0482 600/27 |
| 6,206,821 | B1 | * | 3/2001  | Rhee ....................... A61B 5/048 600/26 |
| 8,465,408 | B2 |   | 6/2013  | Phillips et al. |
| 8,475,354 | B2 |   | 7/2013  | Phillips et al. |
| 8,480,554 | B2 |   | 7/2013  | Phillips et al. |
| 8,585,568 | B2 |   | 11/2013 | Phillips et al. |
| 8,870,737 | B2 |   | 10/2014 | Phillips et al. |
| 8,888,672 | B2 |   | 11/2014 | Phillips et al. |
| 8,888,673 | B2 |   | 11/2014 | Phillips et al. |
| 8,926,490 | B2 |   | 1/2015  | Phillips et al. |
| 8,961,386 | B2 |   | 2/2015  | Phillips et al. |
| 2005/0149144 | A1 | * | 7/2005 | Siever .................. A61M 21/00 607/45 |
| 2008/0033297 | A1 |   | 2/2008 | Sliwa |
| 2009/0082690 | A1 |   | 3/2009 | Phillips et al. |
| 2009/0163976 | A1 |   | 6/2009 | Borckardt et al. |
| 2010/0298623 | A1 |   | 11/2010 | Mishelevich |
| 2011/0196446 | A1 |   | 8/2011 | Wu et al. |
| 2012/0046531 | A1 |   | 2/2012 | Hua |

FOREIGN PATENT DOCUMENTS

| CN | 202096603 U | 1/2012 |
|---|---|---|
| KR | 20090097150 A | 9/2009 |
| WO | WO 99/02217 | 1/1999 |
| WO | WO 2005/118067 A1 | 12/2005 |
| WO | WO 2008/046231 A1 | 4/2008 |
| WO | WO 2008/077440 A1 | 7/2008 |
| WO | WO 2010/113164 A1 | 10/2010 |
| WO | 2010147913 A1 | 12/2010 |

OTHER PUBLICATIONS

Gerdes, Lee et al., "HIREEM™: a noninvasive, allostatic methodology for relaxation and auto-calibration of neural oscillations," *Brain and Behavior*, 2013, 3(2):193-205.
Jorge, Ricardo E. et al., "Treatment of Vascular Depressing Using Repetitive Transcranial Magnetic Stimulation," *Arch Gen Psychiatry*, 2008, 65(3):268-276.
Terao, Yasuo et al., "Shortening of simple reaction time by peripheral electrical and submotor-threshold magnetic cortical stimulation," *Exp Brain Res*, Jul. 1997, 115(3):Abstract.
Gerdes, L., Sung, L., "Brainwave Optimization (High-resolution, Relational, Resonance-based Electroencephalic Mirroring): a Noninvasive Technology for Neuro-oscillatory Calibration." *Brain State Technologies*, 2010, 1-14.
Hoeft, F. et al., "Electronically Switchable Sham Transcranial Magnetic Stimulation (TMS) System." *PLoS ONE*, Apr. 2008, 3(4): 1-10, e1923. DOI:10.1371/journal.pone.0001923.

(Continued)

*Primary Examiner* — Carrie R Dorna
(74) *Attorney, Agent, or Firm* — Saliwanchik, Lloyd & Eisenschenk

(57) ABSTRACT

One or more sensory, auditory and/or visual stimuli are presented to a subject at a specific frequency that is equal to, or a harmonic of, the intrinsic frequency of one or more of the subject's biological signals. The purpose is to indirectly (through the eyes, ears, or touch) provide frequency coupling among different organs (e.g., heart, brain, breathing, and gastrointestinal movement) through rhythmic entrainment. The specific harmonic chosen is the one closest to the interested EEG frequency. The interested frequency is chosen based on the cognitive element or symptom that is targeted. Additionally, games and programs (audio, video, computer) can incorporate Pavlovian cues to facilitate placing the brain in an acceptable state. In one embodiment, the ticking sound of a repetitive transcranial stimulation (rTMS) device is played to subconsciously remind the patient of the rTMS treatment and thereby produce a therapeutic effect. Additionally, physical stimulus such as tapping or low-level electrical stimulation at a predetermined rate will accomplish the same effect.

12 Claims, No Drawings

(56) References Cited

OTHER PUBLICATIONS

Mennemeier, M. et al., "Sham Transcranial Magnetic Stimulation Using Electrical Stimulation of the Scalp." *Brain Stimul.*, Jul. 2009, 2(3): 168-173.
Rossi, S. et al., "Effects of Repetitive Transcranial Magnetic Stimulation on Movement-related Cortical Activity in Humans." *Cerebral Cortex*, Aug. 2000, 10(8): 802-808.
Rossi, S. et al., "A real electro-magnetic placebo (REMP) device for sham transcranial magnetic stimulation (TMS)." *Clinical Neurophysiology*, 2007, 118: 709-716.

* cited by examiner

FREQUENCY SPECIFIC SENSORY STIMULATION

CROSS-REFERENCE TO RELATED APPLICATIONS

The present application claims priority under 35 U.S.C. § 119(e) to U.S. Provisional Applications Nos. 61/621,399, and 61/621,389 filed on Apr. 6, 2012 the disclosures of which are incorporated herein by reference in its entirety.

FIELD OF THE INVENTION

The present invention relates to a method of treating a neuropsychiatric conditions and improving a physical function in a patient in need thereof which comprises subjecting the patient to a sensory stimulation at a frequency of a biological metric or a harmonic thereof. The stimulation can be visual, sound or touch. Additionally, the present invention can be used to provide a conditional, Pavlovian-like response in a patient who has already received a repetitive transcranial magnetic stimulation treatment (rTMS) with an rTMS device by subjecting the patient to (a) audio sounds substantially similar to the sounds emitted by the rTMS device or (b) a physical stimulus produced at a frequency or rate similar to the audio sounds produced by the rTMS device whereby the patient receives therapeutic effects of the original rTMS treatment.

BACKGROUND OF THE INVENTION

Various bodily functions operate at frequencies that are harmonics or sub-harmonics of the brain's intrinsic frequency. For example, the heart rate is approximately the $8^{th}$ or $9^{th}$ sub-harmonic of the brain's alpha frequency at awake and $2^{nd}$ or $3^{rd}$ sub-harmonic of delta at sleep. The breathing rate is the $5^{th}$ sub-harmonic of the heartbeat which is why the standard CPR procedure requires 5 heart compressions for each breath although some now recommend that only compressions be administered to CPR recipients. The gastrointestinal movement frequency is approximately the $4^{th}$ or $5^{th}$ sub-harmonic of the breathing rate.

Transcranial magnetic stimulation (TMS) is a procedure that uses magnetic fields to stimulate nerve cells in the brain to improve symptoms of depression and other neuropsychiatric conditions. Traditionally, TMS coils have been of a circular or figure-8 shape, designed to achieve maximum strength at a single point. For treatment of depression with transcranial magnetic stimulation, a large electromagnetic coil is placed against or near the scalp near the forehead. The electromagnet used in transcranial magnetic stimulation creates electric currents and magnetic fields that stimulate nerve cells in the region of the brain involved in mood control and depression.

Repetitive transcranial magnetic stimulation (rTMS) is a non-invasive, non-surgical method to excite neurons in the brain. Weak electric currents are induced in brain tissues by rapidly changing electro-magnetic fields through electromagnetic induction. Brain activity is triggered and modulated without the need for surgery or external electrodes. In particular, alpha brain waves can be modulated in a desirable manner.

In an rTMS device, current is generated through a wire to a main coil where an electromagnetic field is induced with direction perpendicular to that of the flat surface of the coil. The coil is placed against or in close proximity to specific areas of the patient's head/scalp corresponding to brain regions underneath the skull that are the target of treatment. The electromagnetic field resulting from the current in the coil penetrates the skull and stimulates brain areas underneath, potentially exciting neurons at predetermined frequencies. rTMS/TMS has several effects, stimulating brain structures according to coil placement, changing neuron firing rates, and adjusting blood-flow in the brain. The rTMS device emits a distinctive clicking sound which the patient can hear during an rTMS treatment. Additionally, the patient receiving an rTMS treatment will experience a tapping sensation in their head adjacent to the magnet coils of the rTMS device. rTMS treatment plans are generally started on a daily treatment basis, usually Monday-Friday, although continuous daily treatments can also be employed. After the patient exhibits a noticeable relief in symptoms or a desirable modulation of brain wave activities then the daily treatment are usually reduced gradually to an intermittent treatment regime such as once or twice a week to biweekly to monthly treatments.

It has been unexpectedly discovered that a mental disorder or a physical function in a patient can be treated or improved by subjecting the patient to a sensory stimulation at a frequency of a biological metric or a harmonic thereof. It has also been unexpectedly discovered that patients who have been successfully treated with rTMS develop a Pavlovian response (conditional response) to the clicking sound of the rTMS machine. This conditional response can be utilized in the continued treatment of the patients by subjecting the patients to an audio sound similar to the clicking sound emitted by the rTMS machine to produce a therapeutic effect which can reduce the number of costly rTMS treatments.

SUMMARY OF THE INVENTION

Briefly, in accordance with the present invention, a mental disorder or a physical function in a patient can be treated or improved by subjecting the patient to a sensory stimulation at a frequency of a biological metric or a harmonic thereof. The biological metric can be any measurable biological metric, such as, for example, an EEG frequency, heart rate, respiratory rate, or gastrointestinal movement rate (rate of peristalsis) of the patient. The stimulation can be any visual, sound or touch stimulation such as, for example, a song, music, a movie, a video game, movement of objects on a video screen, flickering lights or a vibration or tapping. The present invention can also produce a conditional therapeutic response in a patient who has received a repetitive transcranial magnetic stimulation treatment (rTMS) with an rTMS device by subjecting the patient to (a) audio sounds substantially similar to the sounds emitted by the rTMS device and/or (b) a physical stimulus produced at a frequency or rate similar to the audio sounds produced by the rTMS device. The patient receives therapeutic effects of the original rTMS treatment. The audio sounds are provided with an analog or digital recording of a ticking sound generated by the rTMS device. In one embodiment, the audio sounds are generated as a possible reward as part of a puzzle, game or task to be used or given by or to the patient.

In one embodiment, the audio sounds are generated as a reward for achieving a goal in a video game. The physical stimulus is provided by an apparatus that produces a tapping or vibration that simulates the tapping sensation felt by a patient undergoing rTMS. The apparatus can be one that is worn by the patient where the tapping or vibration can easily be felt by the patient such as for example a watch, a bracelet, a necklace, hat and a video control unit. In one embodiment the conditional response is elicited by both an audio stimulus and a physical stimulus. Stimulus may also be provided using a low-level electrical pulse through electrodes attached to the skin, which provides a sensation on the skin underneath the electrodes.

Additionally, the present invention relates to devices that produce said sensory stimulation such as audio sounds and/or physical stimuli and/or vibrations. An audio medium produces sounds that include a frequency of a biological metric or a harmonic thereof. Audio media include but are not limited to audio tapes, a digital audio files, video tapes, video games, computer files, smart phones, computer files, MP3 devices, analog and digital video files and DVDs. A visual medium produces a light, flicker or an object's movement in the visual medium that corresponds to a frequency of a biological metric or a harmonic thereof. A physical stimulus device produces a sensation felt by a patient that corresponds to a frequency of a biological metric or a harmonic thereof. Suitable sensations include a tapping sensation, vibrations and electrical stimulation. A physical stimulus device includes watches, bracelets, headbands, hats, caps, necklaces, cell phones, hand-held computers such as tablets and iPads, handheld video control units or any other device that can be programmed to provide a tapping, vibrations and/or electrical stimulus that can be felt by the patient.

DETAILED DESCRIPTION OF THE EMBODIMENTS

In practicing the present invention, providing stimulation (e.g., light, auditory, sensory) at the frequency (or a harmonic thereof) of one of the body's natural biological signals makes use of the body's natural resonance to influence brain activity and will resynchronize the heart/brain/respiratory/gastrointestinal oscillation, lower energy, and increase efficiency and stability. This in turn will lessen the symptoms of medical disorders or improve cognitive function and/or physical function.

Additionally, the present invention provides a conditional therapeutic response, or Pavlovian-like response, in a patient who has received a successful repetitive transcranial magnetic stimulation (rTMS) treatment with an rTMS device by subjecting the patient to (a) audio sounds substantially similar to the sounds emitted by the rTMS device or (b) a physical stimulus produced at a frequency or rate similar to the audio sounds produced by the rTMS device. By subjecting the patient to an audio or physical stimulus similar to audio and physical stimuli experienced by the patient during their rTMS treatments the patient receives therapeutic effects of the original rTMS treatment.

The specific rTMS device used by the treating physician in the original rTMS treatment of the patient does not affect the practice of the present invention. All rTMS devices will produce a distinctive clicking sound and produce a tapping sensation felt by the patient on his/her skull directly opposite the placement of the rTMS coils. Transcranial magnetic stimulation devices are commercially available from MagVenture, Inc. Atlanta, Ga. including MAGPRO compact, MAGPRO® R30, MAGPRO® R100, and MAGPRO® X100.

In preferred embodiments for patients who have not had a prior rTMS treatment, the stimuli may be presented through an entertainment medium, such as a movie, MP3 player, video game, smart cell phone or computer application. Some examples of this may include, but are not limited to the following:

a. Modulate the sounds already present in the medium at the desired frequency (i.e., introduce a warble to the sound).
b. Cause a video screen to flicker slightly at the desired frequency while the subject is viewing it.
c. Vary the movements of items on the screen to match the desired frequency (e.g., the number of steps per minute of a video game character match the desired frequency).
d. Vibrate the controller of a video game at the desired frequency.
e. Require the player of a video game to respond at the desired frequency (e.g., tap the fire button at the desired frequency to score points).

In another embodiment, one can modulate the sounds or light already present in a medium at the desired frequency (i.e., introduce a warble to the sound) according to the present invention. The screen can be directed to flicker slightly at the desired frequency while the subject is viewing it. The movements of items on the screen can be varied to match the desired frequency. eg., the number of steps per minute of a video game character are programmed to match the desired frequency. The controller of a video game can be caused to vibrate at the desired frequency. The player of a video game can be directed to respond at the desired frequency e.g., tap the fire button at the desired frequency to score points. Software is designed to imbed the extra signal in one or multiple channels of a multi-channel audio signal. Usually the first two channels carry the music of choice and the rest of the channels are programmed for other signals according to the present invention, such as, for example, heartbeat at 0.9-2.0 Hz and α-brain wave frequency at 9-13 Hz. Harmonics and sub-harmonics can also be employed. Human ears are not tuned to listen to such low frequencies but when modulated with the audible music, these signals will work as extra tones superimposed on the music. The modulation depth can be adjusted based on a subject's comfort level. Light pulses can also be programmed into a video program to display light at the desired frequencies.

Improved physical performance or functions that can be achieved according to the present invention include concentration, sleep, alertness, memory, blood pressure, stress, libido, speech, motor function, physical performance, cognitive function, intelligence, height (in children) and weight.

Therapeutic effects that can be achieved according to the present invention include mental or neuropsychiatric disorders such as Autism Spectrum Disorder (ASD), Alzheimer's disease, attention deficit hyperactivity disorder (ADHD), schizophrenia, anxiety, depression, coma, Parkinson's disease, substance abuse, bipolar disorder, a sleep disorder, an eating disorder, tinnitus, traumatic brain injury, post traumatic stress syndrome, and fibromyalgia.

In patients that have had a prior rTMS treatment the original rTMS treatment experienced by the patient must have been successful in improving a physical function or alleviating the symptoms of a neuropsychiatric condition in order to produce a conditional response. The exact number of treatments to produce a desired response will vary by patient, the desired physiological function and the underlying neuropsychiatric disease condition. Generally, treatments are started on a daily basis and when improvements in symptoms, physiological functions and/or brain wave activity is observed then the patient can be placed on a maintenance treatment protocol that will involve periodic rTMS treatments such as for example twice weekly, treatments, once a week treatment, bi-weekly treatments and monthly treatments. It is after successful treatment that it has been unexpectedly discovered that patients will develop a conditional response to the audio and physical stimuli that the patient experiences during the rTMS treatments. By exposing the patient to these audio and/or physical stimuli in between maintenance rTMS treatments additional therapeutic effects can be achieved at the fraction of the cost of an rTMS treatment.

Typically, once a patient is on a maintenance rTMS program, audio and/or physical stimuli (tapping, vibrations, electrical stimulation) described herein can be added to the patient's regimen to self administer between regularly scheduled rTMS treatments. The audio and/or physical stimuli produce a conditional response in the patient whereby the patient's physiological functions/performance is enhanced and symptoms of the underlying neuropsychiatric condition are alleviated.

The audio sounds are provided with an analog or digital recording of a ticking sound generated by the rTMS device. In one embodiment, the audio sounds are generated as a part of a puzzle, game or task to be used or given by or to the patient. Preferably, the audio sounds are generated as a reward for achieving a goal in a video game. The physical stimulus is provided by an apparatus that produces a tapping, vibration or electrical stimulation that simulates the tapping sensation felt by a patient undergoing rTMS. The apparatus can be one that is worn by the patient where the tapping, vibration or electrical stimulation can easily be felt by the patient such as for example a watch, a bracelet, a cap, a necklace and a video control unit. In one embodiment the conditional response is elicited by both an audio stimulus and a physical stimulus.

Additionally, the present invention relates to devices that produce said audio sounds and/or physical stimuli. An audio medium produces sounds substantially similar to the sounds emitted by an rTMS device preferably at the same intensity level and frequency as the sounds produced by the rTMS device. Audio media include but are not limited to audio tapes, a digital audio files, video tapes, video games, computer files and DVDs. A physical stimulus device produces a sensation felt by a patient who has undergone an rTMS treatment. Suitable sensations include a tapping sensation, vibrations, and low-level electrical stimulation. A physical stimulus device includes watches, bracelets, necklaces, caps, cell phones, hand-held computers such as tablets and iPads, handheld video control units or any other device that can be programmed to provide a tapping or vibrations stimulus that can be felt by the patient.

Improved physical performance or functions that can be achieved according to the present invention include concentration, sleep, alertness, memory, blood pressure control, stress, libido, speech, motor function, physical performance, cognitive function, intelligence, height (in children) and weight.

Therapeutic effects that can be achieved according to the present invention include Autism Spectrum Disorder (ASD), Alzheimer's disease, ADHD, schizophrenia, anxiety, pain management, depression, coma, Parkinson's disease, substance abuse, bipolar disorder, a sleep disorder, an eating disorder, tinnitus, traumatic brain injury, post traumatic stress syndrome, and fibromyalgia.

The following examples illustrate the practice of the present invention but should not be construed as limiting its scope.

Example 1—Sound Recording to Treat ASD

An audio file is made to make a warbling sound to treat a patient with ASD. The sound is programmed to emit a warbling sound at a frequency of 12 Hz based on the 8th harmonic of the patient's heart rate of 90 (1.5 Hz). The patient is instructed to listen to the audio program several times per day. Favorable changes in alpha brain waves can be determined by conducting periodic EEG readings. The audio file can be programmed to play on an MP3 player, a computer, a cassette tape, a hand held electronic device (cell phone, hand held video game, a television, a stereo system, headphones, and the like. The warble sound is programmed to play continuously for 6 seconds per minute during the entire treatment session for 30 minutes during the entire treatment session for 30 minutes.

Example 2—Sound Recording to Improve Athletic Performance

An audio file is made to make a warbling sound to treat an elite runner. The sound is programmed to emit a warbling sound at a frequency of 12 Hz based on the 12th harmonic of the patient's heart rate of 60 (1 Hz). The patient is instructed to listen to the audio program several times per day and immediately before the runner's event. Enhanced running performance is achieved. The audio file can be programmed to play on an MP3 player, a computer, a cassette tape, a hand held electronic device (cell phone, hand held video game, a television, a stereo system, headphones, MP3 player and the like). The warble sound is programmed to play continuously for 6 seconds per minute during the entire treatment session for 30 minutes.

Example 3—Sound Recording to Treat Alzheimer's Disease

An audio file is made to make a warbling sound to treat a patient with Alzheimer's disease. The sound is programmed to emit a warbling sound at a frequency of 12 Hz based on the 8th harmonic of the patient's heart rate of 90 (1.5 Hz). The patient is instructed to listen to the audio program several times per day and immediately before going to bed at night. The patient will experience improvement in Alzheimer's disease symptoms such as improved short term memory and increased verbal communication. Favorable changes in alpha brain waves can be determined by conducting periodic EEG readings. The audio file can be programmed to play on an MP3 player, a computer, a cassette tape, a hand held electronic device (cell phone, hand held video game, a television, a stereo system, headphones, MP3 player and the like). The warble sound is programmed to play continuously for 6 seconds per minute during the entire treatment session for 30 minutes.

Example 4—Sound Recording to Treat ADHD

An audio file is made to make a warbling sound to treat a patient with ADHD. The sound is programmed to emit a warbling sound at a frequency of 10 Hz based on the 8th harmonic of the patient's heart rate of 75 (1.25 Hz). The patient is instructed to listen to the audio program several times per day and immediately before going to bed at night. The patient will experience improvement in ADHD including increased focus and concentration. Favorable changes in alpha brain waves can be determined by conducting periodic EEG readings. The audio file can be programmed to play on an MP3 player, a computer, a cassette tape, a hand held electronic device (cell phone, hand held video game, a television, a stereo system, headphones, MP3 player and the like). The warble sound is programmed to play continuously for 6 seconds per minute during the entire treatment session for 30 minutes.

Example 5—Sound Recording to Increase Athletic Performance of a Long Distance Runner An audio file is made to make a warbling sound to treat an elite marathon runner. The sound is programmed to emit a warbling sound at a frequency of 11.62 Hz based on the 14th harmonic of the patient's resting heart rate of 50 (0.83 Hz). The patient is instructed to listen to the audio program several times per day and immediately before the runner's event. The patient was also instructed to wear a headband that during the marathon event that produces a tapping or vibration sensation on the runner's head at a frequency of 11.62 HZ. Enhanced running performance is achieved. The audio file can be programmed to play on an MP3 player, a computer, a cassette tape, a hand held electronic device (cell phone, hand held video game, a television, a stereo system, headphones, MP3 player and the like). The warble sound is programmed to play continuously for 6 seconds per minute during the entire treatment session for 30 minutes.

Example 6—Method of Reducing Symptoms and/or Improving Cognition in rTMS Patients Following successful rTMS treatment patients will gain benefit of a temporary reduction in symptoms and improvement in cognitive performance by listening to a ticking sound that resembles the ticking sound of rTMS machine at a frequency set to the frequency of the rTMS machine during their initial treatment.

Example 7—Audio File Programmed to Emit Sound of an rTMS Device to Improve Performance A competitive female mountain biker was treated with rTMS to improve her focus and concentration for upcoming races. The mountain biker was given an audio file program to play before each race. The audio file included a ticking sound at a frequency that reminded her of the rTMS treatment. She said that this helped her to focus and concentrate similar to the results from the actual rTMS treatments.

Example 8—Calming Autistic Patients with rTMS Sound Stimulation

Several autistic patients are calmed by the sound of the rTMS machine set at the frequency of their rTMS treatment, even if the sound is a recording and they are getting no actual treatment at all.

Example 9—Video Game that Stimulates the Sound of an rTMS Device

A video game that has several playing levels based on the skill of the player is programmed to simulate the ticking sound (preferably at the frequency of the rTMS treatment that a patient received) of an rTMS device after each level is mastered and before the next level starts. The simulated sound and frequency of the rTMS device produces effects in the patient similar to the effects that the patient received from his/her original rTMS treatment. The video game can be played on a computer, a video game terminal or a hand held device.

Example 10—Word Search Game that Stimulates the Sound of an rTMS Device

An electronic word search game where words are identified out of a matrix of letters is programmed to simulate the sound of an rTMS device after each word is successfully identified. The sound is preferably broadcast at the same frequency as the frequency of a patient's rTMS treatment. The simulated sound and frequency of the rTMS device produces effects in the patient similar to the effects that the patient received from his/her original rTMS treatment. The word search game can be played on a computer, a video game terminal or a hand held device.

In other embodiments of the present invention, patients that have been successfully treated with rTMS to improve physical functions or treat neuropsychiatric conditions will obtain a therapeutic benefit or an improved physical performance or function by being exposed to a stimulus that is substantially similar to a sound or feeling the patient experienced undergoing the original rTMS treatments. Preferably, the patients are exposed to sounds, electrical stimulation, tapping, vibrations that emulate the sounds, tapping or vibrations experienced during the rTMS treatment. Additionally, in further embodiments, patients who have not received prior rTMS treatment can receive therapeutic benefits for a mental disorder or for improving a physical function by being subjected to a sensory stimulation at a frequency of a biological metric or a harmonic thereof. The stimulation can be visual, sound or touch.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A method of treating a mental disorder in a patient in need thereof which comprises detecting a single frequency of a non-EEG biological metric of a patient, subjecting a left hemisphere and a right hemisphere of the patient's brain to at least one sensory stimulation signal at only the single frequency, or only a harmonic thereof, of the non-EEG biological metric, wherein the left and right hemispheres are subjected to only one of the single frequency and the harmonic thereof throughout an entire treatment session and wherein the frequency of the stimulation signal is within an Alpha electroencephalography (EEG) band of the patient.

2. The method of claim 1 wherein the non-EEG biological metric is a heart rate, respiratory rate, or gastrointestinal rate of peristalsis of the patient.

3. The method of claim 1 wherein the sensory stimulation signal is delivered by sound, visual media or touch.

4. The method of claim 3 wherein the sensory stimulation signal is embedded into a song, music, a movie, a video game, a movement of objects on a video screen, an audio file, flickering lights, or a vibration.

5. The method of claim 1 wherein the mental disorder is Autism Spectrum Disorder (ASD), Alzheimer's disease, Attention Deficit Hyperactivity Disorder (ADHD), schizophrenia, anxiety, depression, coma, Parkinson's disease, substance abuse, bipolar disorder, a sleep disorder, an eating disorder, tinnitus, traumatic brain injury, or fibromyalgia.

6. A method of improving a physical condition in a patient in need thereof which comprises detecting a single frequency of a non-EEG biological metric of a patient, subjecting a left hemisphere and a right hemisphere of the patient's brain to at least one sensory stimulation signal at only the single frequency, or only a harmonic thereof, of the non-EEG biological metric, wherein the left and right hemispheres are subjected to only one of the single frequency and the harmonic thereof throughout an entire treatment session, and wherein the frequency of the stimulation signal is within an Alpha electroencephalography (EEG) band of the patient.

7. The method of claim 6, wherein the sensory stimulation signal is a single color throughout an entire treatment session.

8. The method of claim 6 wherein the non-EEG biological metric is a heart rate, respiratory rate, or gastrointestinal rate of peristalsis of the patient.

9. The method of claim 6 wherein the sensory stimulation signal is delivered by sound, visual media, or touch.

10. The method of claim 9 wherein the sensory stimulation signal is embedded into a song, music, a movie, a video game, a movement of objects on a video screen, an audio file, flickering lights, or a vibration.

11. The method of claim 6 wherein the physical condition comprises concentration, sleep, alertness, memory, blood pressure, stress, libido, speech, motor function, physical performance, cognitive function, intelligence, height, or weight.

12. The method of claim 1, wherein the sensory stimulation signal is a single color throughout an entire treatment session.

* * * * *